(12) United States Patent
Elliott (10) Patent No.: US 8,541,464 B2
(45) Date of Patent: Sep. 24, 2013

(54) TREATMENT OF ATRIAL FIBRILLATION (75) Inventor: Gary T. Elliott, Portland, ME (US)

(73) Assignee: HUYA Biosciences International LLC, San Diego, CA (US)

( * ) Notice: Subject to any disclaimer, the term of this patent is extended or adjusted under 35 U.S.C. 154(b) by 0 days.

(21) Appl. No.: 13/509,752

(22) PCT Filed: Nov. 16, 2010

(86) PCT No.: PCT/US2010/056857
§ 371 (c)(1),
(2), (4) Date: May 14, 2012

(87) PCT Pub. No.: WO2011/062906
PCT Pub. Date: May 26, 2011

(65) Prior Publication Data
US 2012/0309810 A1 Dec. 6, 2012

Related U.S. Application Data (60) Provisional application No. 61/261,925, filed on Nov. 17, 2009.

(51) Int. Cl.
*A61K 31/4025* (2006.01)

(52) U.S. Cl.
USPC .......................................... 514/422

(58) Field of Classification Search
None
See application file for complete search history.

(56) References Cited

U.S. PATENT DOCUMENTS

2012/0245214 A1* 9/2012 Elliott ........................ 514/422

* cited by examiner

*Primary Examiner* — Raymond Henley, III
(74) *Attorney, Agent, or Firm* — Foley & Lardner LLP (57) ABSTRACT Atrial fibrillation (AF) can be treated or prevented by administering to a subject who suffers from or is at risk of suffering from AF a composition comprised of an amount of an active agent, which is 4-methoxy-N-(3,5-bis(1-pyrrolidinyl)-4-hydroxy benzyl)benzene sulfonamide (sulcardine) or a pharmaceutically acceptable salt thereof, such that the Cmax value the active agent in the subject is in the range from about 1 μM to about 20 μM.

14 Claims, 2 Drawing Sheets

TREATMENT OF ATRIAL FIBRILLATION

CROSS-REFERENCE TO RELATED PATENT APPLICATIONS

This application claims priority to U.S. provisional application No. 61/261,925, filed Nov. 17, 2009, the entire contents of which are incorporated herein by reference.

FIELD OF INVENTION

This invention relates to treating atrial fibrillation (AF) with 4-methoxy-N-(3,5-bis-(1-pyrrolidinyl)-4-hydroxy benzyl)benzene sulfonamide (sulcardine) or a pharmaceutically acceptable salt of sulcardine.

BACKGROUND OF THE INVENTION

Throughout this disclosure, various publications, patents and published patent specifications are referenced by an identifying citation. The disclosures of these publications, patents and published patent specifications are hereby incorporated by reference in their entirety into the present disclosure, thereby to describe the state of the art to which this invention pertains.

Cardiac arrhythmia, also known as "dysrhythmia," is a rubric for a group of conditions characterized by abnormal electrical activity in the heart. Examples of arrhythmias include premature ventricular contractions, ventricular tachycardia, ventricular fibrillation and supraventricular tachyarrhythmia such as atrial fibrillation. By example, atrial fibrillation (AF) is a supraventricular tachyarrhythmia characterized by uncoordinated atrial activation with consequent deterioration of atrial mechanical function. Persistent and/or chronic AF is associated with increased risk of thromoembolic events including MI and stroke and heart failure. Theories of the mechanism of AF involve two main processes: enhanced automaticity in one or several rapidly depolarizing foci and reentry involving one or more circuits.

AF is the most common arrhythmia requiring medical care, with a prevalence of almost 1% in the adult U.S. population (projection of 6 million in U.S. in 2006 and 9 million by 2020). Its prevalence increases with age, such that 8% of people >80 years old have AF. As U.S. and European demographics shift toward an older population, AF will become an even more prevalent cardiovascular disease. Recurrent episodes of AF occur in patients on average 50%/year. Accordingly, AF is a major strain on the health care system, with an average cost in the United States of $3600 per case per annum.

AF is associated with symptoms which adversely affect quality of life including, for example, shortness of breath, chest discomfort or pain and exercise intolerance. The longer the patient remains in AF the greater the risk of thrombus formation in the atria and hence risk of thromboembolic stroke, and hence the need for chronic anticoagulant therapy. It is felt that a large percentage of all stroke cases in the U.S. are secondary to persistent or chronic AF. Other serious cardiac events occurring at significantly higher incidence in AF patients include heart failure and myocardial infarction (MI).

Treatment of AF revolves around cardioversion and use of anticoagulents in persistent and chronic cases. Cardioversion of patients with acute symptomatic AF or paroxsysmal AF can be achieved by means of the use of antiarrhythmic drugs (AADs) or electrical cardioversion to restore sinus rhythm (SR). Alternatively, the physician may elect to simply control rate using drugs which slow AV node conduction and hence control ventricular response rate in patients with AF.

A large controversy currently exists as to whether rhythm control is superior to rate control of patients, although most opinion leaders would prefer their patients be in SR and have no need for anticoagulation. Studies evaluating incidence of serious cardiovascular (CV) sequeli or death with either approach are at this time inconclusive. Cardioversion by defibrillation is not a trivial undertaking, requiring patients to be sedated under the case of an anesthesiologist first and is associated with significant incidence of muscle pain and skin burns. Anti-arrhythmic drugs fall into a number of pharmacologic classes based on the mechanism of actions. There are five recognized AAD classes:

Class I: Na-channel blockers
Class II: Beta-blockers
Class III: K-channel blockers
Class IV: Ca-channel blockers
Class V: Miscellaneous (adenosine, digoxin, etc.)

The development of new anti-AF drugs has unfortunately, at this point, not increased the popularity of pharmacological cardioversion due to low efficacy rates, the risks of drug-induced torsades de pointes (TdeP), ventricular tachycardia, or other serious arrhythmias associated with currently available agents. Pharmacological cardioversion is still less effective than electrical cardioversion and, hence, defibrillation remains the mainstay of treatment of refractory acute atrial fibrillation.

Most marketed agents, e.g., propofenone, flecanide and ibutalide, carry risk of inducing TdeP; hence, most of these agents are not recommended for use in patients suffering from any of and having history of any of ischemic heart disease, prior MI, and prolonged QT syndrome. A number of these agents, such as sotalol, flecanide, propafenone and dronadarone, also display negative effects on contractility of the heart, making them contraindicated in heart failure. The most common severe adverse event is a pro-arrhythmic effect, which is usually associated with blockade of the human Ether-á-go-go-related gene (hERG)-encoded potassium channel $I_{Kr}$, resulting in QT-interval prolongation and potentially fatal ventricular arrhythmia TdeP. Notably, Na-channel blockers that lack inhibitory activity on $I_{Kr}$ also may be highly pro-arrhythmic (flecanide) in association with their ability to increase action potential duration, leading to Ca overload in a pronounced fashion and inducing re-entry rhythms.

Although anti-arrhythmic agents such as Na-channel blockers (Class I), Ca-channel blockers (Class IV) and beta-blockers (Class II), and digoxin and adenosine (Class V) all have some anti-AF properties, Class III anti-arrhythmic agents, which are all K-channel inhibitors and by recent consensus of medical experts mixed-channel blockers, are preferred for the anti-AF indication due to their perceived safety advantage and potency in atrial arrhythmia. Recurrent acute AF, persistent AF and paroxsysmal AF eventually lead to the development of chronic AF, there is electrical remodeling in atrial tissue, an adaptive response wherein the relative contributions of different atrial expressed ion channels change. This alteration in channel trafficking is manifested by the shortening of action potential (AP) duration, with a relatively greater contribution from the ultra rapid potassium current $I_{Kur}$, the transient outward potassium current $I_{to}$, and the muscarinic acetylcholine potassium current $I_{KAch}$, as well as a decreased influence of the delayed rectifying potassium current, which has two components: rapid [$I_{Kr}$] and slow [$I_{Ks}$]) and the calcium current. Chronic AF is intractable to medical intervention and maintaining SR in these patients is very difficult; leading to the statement that AF begets AF.

Currently available AADs that target potassium channels tend to block the late Phase 3 repolarizing currents, $I_{Kr}$, and $I_{Ks}$, which may make them less effective during AF because Phase 3 is shortened by chronic AF, although this hypothesis has not been proven with certainty. Currently available AADs also target the same ion channels in the ventricle, which can prolong the QT interval, resulting in enhanced risk of TdeP. AADs with selectivity for the atrial specific channels ($I_{Kur}$, $I_{to}$, $I_{KAch}$), which are more active after the electrical remodeling of AF, might provide effective rhythm control with minimal ventricular pro-arrhythmic risk, although down regulation of at least one of these atrial selective channels, $I_{KAch}$, has been reported with persistent/chronic AF.

Sulcardine, 4-methoxy-N-(3,5-bis-(1-pyrrolidinyl)-4-hydroxy benzyl)benzene sulfonamide, and its salts, such as sulcardine sulfate, constitute a group of new chemicals with potent anti-arrhythmic activity. Sulcardine is a multi-ion (fast and slow Na, L-Ca, and $K_{Ito}$) channel blocker and represents what may be the sole example of a substituted sulfonamide class of anti-arrhythmic. Sulcardine salts can be used as an intravenous injectable or as oral doses for the treatment of arrhythmias, including supraventricular tachyarrhythmia, premature ventricular contractions, ventricular tachycardia and ventricular fibrillation.

In addition, the evidence to date suggests that one advantage of sulcardine and salts is that they lack significant pro-arrhythmic activity, as demonstrated in rigorous preclinical safety models, including a post-MI sudden-death conscious canine model and the validated rabbit ventricular wedge model. Additionally, it has been shown that they do not increase defibrillation threshold, nor increase defibrillation failure risk in a post-MI canine model as was seen with flecanide. On the basis of these data, sulcardine and salts, with their very low apparent pro-arrhythmic potential, could potentially be used to treat acute and recurrent atrial fibrillation in the presence of organic heart disease, prolonged QR syndrome, and ventricular arrhythmias, including premature ventricular contractions (PVCs), ventricular tachycardia (VT), and ventricular fibrillation (VF), in either acute- or chronic-administration settings owing to their ability to be formulated into intravenous and oral dosing formulations.

SUMMARY OF THE INVENTION

It has been reported that, with respect to human atrial cardiomyocytes in vitro, sulcardine and its salts display IC50 values in the range of 26-100 µM. These findings indicated that an effective pharmacologic blockade of ion channels in vivo required reaching concentrations in excess of these IC50 values, probably several multiples thereof, to elicit an anti-arrhythmic effect. Yet, plasma concentrations of sulcardine sulfate that are close to or higher than this indicated IC50 range were determined to be associated with hypotension, QT prolongation, and undesirable effects on ventricular contractility, inter alia. Accordingly, there was an expectation that it would be infeasible to achieve blood concentrations of sulcardine that are effective against AF without engendering untoward side effects.

Contrary to this expectation, the invention allows for treatment of AF, using sulcardine or pharmaceutically acceptable salt of sulcardine, without the incidence of these side effects. In accordance with one aspect of the invention, therefore, a method for treating AF is provided that comprises administering to a subject who suffers from or is at risk of suffering from AF a composition comprised of an amount of an active agent, which is 4-methoxy-N-(3,5-bis-(1-pyrrolidinyl)-4-hydroxy benzyl)benzene sulfonamide (sulcardine) or a pharmaceutically acceptable salt thereof, such that the maximum steady state plasma concentration (Cmax) of the active agent in the subject ranges between about 1 µM to about 20 µM. The invention also contemplates such a treatment where the Cmax of the active agent is in the range from about 0.1 µM, 0.5 µM, 1 µM, 2 µM, 3 µM, 4 µM or 5 µM to about 25 µM, 20 µM, 18 µM, 15 µM, 12 µM, 10 µM, 9 µM, 8 µM, 7 µM or 6 µM.

DETAILED DESCRIPTION OF THE INVENTION

Throughout this application, the text refers to various embodiments of the inventive compounds, compositions, and methodology. The various embodiments described are representative examples and should not be construed as descriptions of alternative species. Rather, the descriptions provided here may be of overlapping scope. The embodiments discussed are illustrative only and are not meant to limit the scope of the present invention.

I. DEFINITIONS

Unless indicated otherwise, the terms and phrases used in this description have the following meanings:

"Treat," "treatment," and "treating" are employed in this description to refer to administering a pharmaceutical composition or formulation for prophylactic and/or therapeutic purposes. The term "therapeutic treatment" refers to administering treatment to a patient already suffering from a condition such as arrhythmia. Thus, in preferred embodiments, treating is the administration to a mammal of therapeutically effective amounts of an anti-arrhythmic agent.

A "subject" of treatment is a prokaryotic or a eukaryotic cell, a tissue culture, a tissue or an animal, e.g., a mammal, including a human. Non-human animals subject to treatment include, for example, a simian, a murine, a canine, a leporid, such as a rabbit, livestock, sport animals, and pets.

An "anti-arrhythmic agent," as used herein, refers to a molecule having a therapeutic effect of treating arrhythmia or alleviating associated symptoms in a subject. Non-limiting examples of arrhythmias include supraventricular tachyarrhythmia such as atrial fibrillation, premature ventricular contractions, ventricular tachycardia, and ventricular fibrillation. In one aspect, an anti-arrhythmic agent is 4-methoxy-N-(3,5-bis-(1-pyrrolidinyl)-4-hydroxy benzyl)benzene sulfonamide (sulcardine) or a pharmaceutically acceptable salt thereof. In another aspect, an anti-arrhythmic agent is sulcardine sulfate.

In accordance with this invention, a pharmaceutically acceptable salt of sulcardine, 4-methoxy-N-(3,5-bis-(1-pyrrolidinyl)-4-hydroxy benzyl)benzene sulfonamide, can be the active agent in a formulation useful for treating arrhythmia. Illustrative of such sulcardine salts are: (A) inorganic acid salts such as acetate, borate, bicarbonate, sulfate, hydrochloride, bromides, chlorides, iodide, hydrobromide, hydroiodide, nitrate, phosphate, diphosphate, and fluorophosphate salts; (B) organic acid salts such as amsonate (4,4-diaminostilbene-2,2-disulfonate), bitartrate, butyrate, citrate, calcium edetate, camsylate, edisylate, estolate, esylate, glutamate, gluconate, gluceptate, lactate, lactobionate, laurate, malate, maleate, mandelate, methylbromide, methylnitrate, methylsulfate, mucate, oleate, oxalate, palmitate, pamoate (1,1-methene-bis-2-hydroxy-3-naphthoate, einbonate), pamoate, pantothenate, salicylate, stearate, subacetate, succinate, sulfate, sulfosalicylate, suramate, propionate, valerate, fiunarate, fumarate, and tartrate salts; and (C) alkali metal salts and alkali earth salts, such as the sodium, potassium, lithium and calcium salts of sulcardine. In this context, a pharmaceutically acceptable salt can have more than one charged atom in its structure and, hence, one or more counterions.

The phrases "effective amount," "therapeutically effective amount," and "pharmaceutically effective amount" denote an amount of an active agent, such as an anti-arrhythmic agent as presently disclosed, that has a therapeutic effect. The doses of the active agent which are useful in treatment are therapeutically effective amounts. Thus, a therapeutically effective amount is an amount of the active agent that produces the desired therapeutic effect, as judged by clinical trial results and/or model animal studies. In particular embodiments, the active agent is administered in a pre-determined dose; hence, a therapeutically effective amount would be an amount of the dose administered. This amount and the amount of the anti-arrhythmic agent can be determined routinely, by conventional methodology, and will vary as a function of different factors, such as the particular arrhythmic event involved. This amount also can depend upon the patient's height, weight, sex, age and medical history.

A "carrier" or "excipient" is a compound or material used to facilitate administration of the compound, for example, to control the release and/or bioavailability of the compound. Solid carriers include, e.g., starch, lactose, dicalcium phosphate, sucrose, and kaolin. Liquid carriers include, e.g., sterile water, saline, buffers, non-ionic surfactants, and edible oils such as oil, peanut and sesame oils. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); GOODMAN AND GILMAN'S: THE PHARMACOLOGICAL BASIS OF THERAPEUTICS, 8th Ed., Pergamon Press.

The phrases "pharmaceutically acceptable carrier" and "pharmaceutically acceptable excipient" can note any and all solvents, dispersion media, coatings, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. Suitable pharmaceutically acceptable excipients include, but are not limited to, buffers, diluents, tonicity agents, stabilizers, antioxidants, preservatives and mixtures thereof.

The term "buffer" denotes a pharmaceutically acceptable excipient, which stabilizes the pH of a pharmaceutical preparation. Suitable buffers are well known in the art and can be found in the literature. Pharmaceutically acceptable buffers comprise but are not limited to glycine-buffers, histidine-buffers, citrate-buffers, succinate-buffers and phosphate-buffers. Independently from the buffer used, the pH can be adjusted at a value from about 2 to about 9, or alternatively from about 2.5 to about 7, or alternatively from about 3 to about 5 or alternatively about 3 with an acid or a base known in the art, e.g., succinic acid, hydrochloric acid, acetic acid, phosphoric acid, sulfuric acid and citric acid, sodium hydroxide and potassium hydroxide. Suitable buffers include, without limitation, glycine buffer, histidine buffer, 2-morpholinoethanesulfonic acid (MES), cacodylate, phosphate, acetate, succinate, and citrate. In one aspect, the buffer is a glycine buffer. In another aspect, the buffer is a histine buffer. The concentration of the buffer can be between about 1 mM and about 100 mM, or alternatively about 2 mM to about 40 mM, or alternatively about 5 mM to about 20 mM.

The terms "diluent," "filler," "dilutant" and "thinner" refer to an inactive ingredients that are added to tablets or capsules in addition to the active drug. A diluent may be used as binders, disintegrants (help the tablet break apart in the digestive system), or flavor enhancers. In one aspect, a diluent is solid, such as starch, cellulose derivatives, and magnesium stearate. In another aspect, a diluent is liquid, such as water, saline, and a dextrose solution (e.g., 5%).

The phrase "tonicity agent" denotes the category of pharmaceutically acceptable agents used to modulate the tonicity of the formulation. Isotonicity generally relates to the osmotic pressure relative to a solution, usually relative to that of human blood serum. A formulation can be hypotonic, isotonic or hypertonic. In one aspect, the formulation is isotonic. An isotonic formulation is liquid or liquid reconstituted from a solid form, e.g., from a lyophilized form and denotes a solution having the same tonicity as some other solution with which it is compared, such as physiologic salt solution and the blood serum. Suitable isotonicity agents include but are not limited to sodium chloride, potassium chloride, mannitol, sucrose, glycerin and any component from the group of amino acids, sugars, as defined herein as well as combinations thereof. In some embodiments, mannitol is present in a concentration of from about 1% to about 20% (w/v %), or alternatively from about 2% to about 10% or alternatively from about 2.5% to about 5%. In one aspect, mannitol is present at about 3%.

The term "stabilizer" denotes a pharmaceutical acceptable excipient, which protects the active pharmaceutical ingredient and/or the formulation from chemical and/or physical degradation during manufacturing, storage and application. Stabilizers include but are not limited to sugars, amino acids, polyols, surfactants, antioxidants, preservatives, cyclodextrines, e.g., hydroxypropyl-β-cyclodextrine, sulfobutylethyl-β-cyclodextrin, β-cyclodextrin, polyethyleneglycols, e.g., PEG 3000, 3350, 4000, 6000, albumin, e.g., human serum albumin (HSA), bovine serum albumin (BSA), salts, e.g., sodium chloride, magnesium chloride, calcium chloride, chelators, e.g., EDTA. In one aspect, a stabilizer is selected from the group consisting of soldium sulfite, sodium bisulfate, sodium metabisulfate, ascordib acid, sodium chloride, EDTA, dextrose, sorbitol, polyethylene glycol (PEG), glycerol and combinations thereof.

In the present context, the term "surfactant" refers to a pharmaceutically acceptable organic substance having amphipathic structures; namely, it is composed of groups of opposing solubility tendencies, typically an oil-soluble hydrocarbon chain and a water-soluble ionic group. Surfactants can be classified, depending on the charge of the surface-active moiety, into anionic, cationic, and nonionic surfactants. Surfactants are often used as wetting, emulsifying, solubilizing, and dispersing agents for various pharmaceutical compositions and preparations of biological materials. In some embodiments of the pharmaceutical formulations described herein, the amount of surfactant is described a percentage expressed in weight/volume percent (w/v %). Suitable pharmaceutically acceptable surfactants include but are not limited to the group of polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), or sodium dodecyl sulphate (SDS). Polyoxyethylenesorbitan-fatty acid esters include polysorbate 20, (sold under the trademark Tween 20™) and polysorbate 80 (sold under the trademark Tween 80™). Polyethylene-polypropylene copolymers include those sold under the names Pluronic© F68 or Poloxamer 188™. Polyoxyethylene alkyl ethers include those sold under the trademark Brij™. Alkylphenolpolyoxyethylene ethers include those sold under the tradename Triton-X. When polysorbate 20 (Tween 20™) and polysorbate 80 (Tween 80™).

An "antioxidant" refers to a molecule capable of slowing or preventing the oxidation of other molecules. Oxidation is a chemical reaction that transfers electrons from a substance to an oxidizing agent. Oxidation reactions can produce free radicals, which start chain reactions that destabilize the product therapeutics and ultimately affect the product activity. Antioxidants terminate these chain reactions by removing free radical intermediates, and inhibit other oxidation reactions by being oxidized themselves. As a result, antioxidants are often reducing agents, chelating agent and oxygen scavengers such as thiols, ascorbic acid or polyphenols. Non-limiting examples of antioxidants include ascorbic acid (AA, E300), thiosulfate, methionine, tocopherols (E306), propyl gallate (PG, E310), tertiary butylhydroquinone (TBHQ), butylated hydroxyanisole (BHA, E320) and butylated hydroxytoluene (BHT, E321).

A "preservative" is a natural or synthetic chemical that is added to products such as foods, pharmaceuticals, paints, biological samples, wood, etc. to prevent decomposition by microbial growth or by undesirable chemical changes. Preservative additives can be used alone or in conjunction with other methods of preservation. Preservatives may be antimicrobial preservatives, which inhibit the growth of bacteria and fungi, or antioxidants such as oxygen absorbers, which inhibit the oxidation of constituents. Common antimicrobial preservatives include, benzalkonium chloride, benzoic acid, cholorohexidine, glycerin, phenol, potassium sorbate, thimerosal, sulfites (sulfur dioxide, sodium bisulfite, potassium hydrogen sulfite, etc.) and disodium EDTA.

II. MODES OF CARRYING OUT THE INVENTION

It has been reported that, in human atrial cardiomyocytes, sulcardine and salts displayed IC50s in the range of 26-100 µM. Based on these findings, it is believed that effectively pharmacologic blockade of ion channels in vivo requires reaching concentrations in excess of these IC50 values, perhaps 2 to 3 fold above these values, to elicit an antiarrhythmic effect.

It has now been discovered that plasma concentrations of sulcardine sulfate close to or higher than the IC50 range are associated with side effects including hypotension, QT prolongation and effects on ventricular contractility. For examples, a 13.6 µM Cmax in minipigs, a 21 µM Cmax in primates and a 25 µM Cmax in dogs led to observed side effects such as hypotension. Therefore, it is appreciated by the one of skill in the art that it is not possible to achieve blood concentrations of sulcardine sulfate that are effective on AF without causing untoward side effects. The current invention, however, provides methods of treating AF with sulcardine or pharmaceutically acceptable salts without causing these side effects.

One aspect of the invention provides a method of treating atrial fibrillation (AF), comprising administering to a subject who suffers from or is at risk of suffering from AF a composition comprised of an amount of an active agent that is 4-methoxy-N-(3,5-bis-(1-pyrrolidinyl)-4-hydroxy benzyl) benzene sulfonamide (sulcardine) or a pharmaceutically acceptable salt thereof, such that the maximum steady state plasma concentration (Cmax) of said active agent in said subject is in the range from about 1 µM to about 20 µM. Alternatively, the Cmax of the active agent in the subject is in the ranger from about 0.1 µM, 0.5 µM, 1 µM, 2 µM, 3 µM, 4 µM or 5 µM to about 25 µM, 20 µM, 18 µM, 15 µM, 12 µM, 10 µM, 9 µM, 8 µM, 7 µM or 6 µM.

The goal of pharmacologic therapy for the treatment of AF depends on whether one is treating acute or paroxysmal AF, to induce rapid cardioversion to a normal sinus rhythm, or whether one seeks to prevent AF recurrence with prolonged administration of the drug. In acute or paroxysmal AF in patients who do not have a history of frequent recurrence, the goal it to acutely induce the pharmacologic cardioversion of a patient who currently is suffering from an AF episode, typically with the administration of a single drug dose or with administration of a limited number of doses. Alternatively, prevention of recurrent AF episodes requires chronic prophylactic treatment.

It has been discovered that, in the context of treating acute or paroxysmal AF to induce immediate cardioversion, the efficacy of sulcardine and its pharmaceutically acceptable salts is a function of peak plasma concentration, requiring the maintenance of a high plasma level for a minimal period, for example, of minutes to less than one hour in duration, to afford time for cardioversion to a normal sinus rhythm; after that time, the patient should remain in normal sinus rhythm without the need for continued therapeutic plasma levels of drug, unless some other precipitating event causes a future recurrence of the arrhythmia. These types of patients who have no or only limited prior history of AF episodes have lower risk of recurrence; hence, continued drug therapy following cardioversion is not indicated. For the acute or paroxysmal AF indication, it is unnecessary to maintain steady blood levels of the drug (steady drug concentration area under the plasma-time curve) for prolonged periods of time, to prevent recurrence of AF over days to months to years at a time. The use of the drug in this clinical situation is akin to the use of electrical cardioversion to acutely drive the heart back into a normal sinus rhythm.

It also has been discovered that the efficacy of sulcardine and its pharmaceutically acceptable salts in the treatment of patients with persistent or frequently recurring AF is a function of the area under the plasma-time curve, rather than of a peak plasma concentration. These patients, with a significant history of prior AF and frequent recurrence, are at much higher risk of recurrence that the acute cohort described above. The atria appear to remodel following frequent or prolonged (chronic) AF episodes, predisposing the patient to a higher risk of future events. As the clinicians say; AF begets AF.

Prevention of recurrent AF in such chronic AF patients requires maintaining drug concentration peak and trough concentrations over the dosing period within a range that minimizes the risk of adverse events, associated with high plasma concentrations, and yet that maintains blood levels above some minimally pharmacologically active concentration. Accordingly, in the treatment of both acute/paroxysmal and recurrent AF, administering active agent over a longer period, e.g., by means of a controlled release formulation or by slow intravenous infusion, has a role to play. In the acute/ paroxysmal AF medical setting, the goal is to achieve rather high blood levels for a period of minutes out to an hour or two, allowing the heart sufficient time to respond to drug therapy and slip back into a normal sinus rhythm. Loading the drug by a continuous, short-term infusion over this period, as opposed to administering the drug by a rapid IV push, blunts peak plasma concentrations, minimizing the risk of hypotension, while allowing for the achievement of high blood levels over a period of time sufficient to result in cardioversion.

Conventional techniques exist for measuring Cmax of an agent, as the accompanying examples illustrate. Further, the Cmax of an active agent can be determined by the amount of the active agent administered to a subject, the characteristics of the subject, route of administration and other pertinent information. Accordingly, in one aspect of the above embodiments of the invention, the amount of the active agent administered is lower than about 90 mg/kg, about or alternatively lower than about 80 mg/kg, about 70 mg/kg, about 60 mg/kg, about 50 mg/kg, about 40 mg/kg, about 30 mg/kg, about 20 mg/kg, about 10 mg/kg, about 9 mg/kg, about 8 mg/kg, about 7 mg/kg, about 6 mg/kg, about 5 mg/kg, about 4 mg/kg, about 3 mg/kg, about 2 mg/kg, about 1 mg/kg, about 0.7 mg/kg, about 0.5 mg/kg, about 0.3 mg/kg, about 0.2 mg/kg or about 0.1 mg/kg. In another aspect, the amount of the active agent administered is from about 0.1 mg/kg to about 90 mg/kg, from about 0.5 mg/kg to about 80 mg/kg, from about 1 mg/kg to about 70 mg/kg, from about 3 mg/kg to about 30 mg/kg, or from about 5 mg/kg to about 10 mg/kg.

The amount of the active agent administered will depend in part on the characteristics of the subject, including without limitation the species, gender and age of the subject. Various mathematical algorithms exist for effecting a conversion of administered amounts, e.g., between different species, as described, for instance in GUIDANCE OF INDUSTRY—ESTIMATING THE MAXIMUM SAFE STARTING DOSE IN INITIAL CLINICAL TRIALS FOR THERAPEUTICS IN ADULT HEALTHY VOLUNTEERS, U.S. Department of Health and Human Services, Food and Drug Administration, Center for Drug Evaluation and Research (July 2005), accessible at www.fda.gov/Drugs/GuidanceCompliance-RegulatoryInformation/Guidances/ucm065014.htm. Thus, 1 mg/kg of the active agent in dog is equivalent to about 0.54 mg/kg in human, and 0.3 mg/kg of the active agent in dog is equivalent to about 0.16 mg/kg in human.

Additionally, the conversion rates between the amount of the active agent and Cmax and AUC can be experimentally determined for a given route and manner of administration. Such determinations are conventional in the field.

As noted above, the active agent of a formulation of the invention can be a pharmaceutically acceptable salt of sulcardine, 4-methoxy-N-(3,5-bis-(1-pyrrolidinyl)-4-hydroxy benzyl)benzene sulfonamide. The preparation of such salts is illustrated by way of the reaction chemistries described below.

1. Reaction of Sulcardine with an Organic or Inorganic Acid

Amines, such as the tertiary amine $R_3N$, react with strong inorganic acids such as hydrochloric acid, hydrobromic acid or hydroiodic acid, to give the corresponding ammonium salt $R_3NH^+X^-$, where X is Cl, Br, or I. Generally, this reaction is carried out by dissolving the amine in an aqueous solvent followed by the addition of a slight excess of the strong acid to the amine. In a typical protocol, sulcardine is dissolved in an aqueous or aqueous-alcoholic solvent, which then is cooled by placing the flask in an ice bath. To the cold stirring solution is added drop-wise a slight excess of the strong acid. After the addition of the acid, the reaction mixture is brought to room temperature and concentrated to precipitate the corresponding salt, which can be separated by filtration. The addition of around 1.1 equivalents of a strong acid results in the formation of a mono-salt of sulcardine, while the bis salt is readily obtained by the addition of around 2.1 equivalents of a strong acid.

Organic acid salts of sulcardine, such as an acetate salt, can be synthesized by passing the compound through a reverse-phase, high-pressure liquid chromatography column, using an aqueous-organic solvent system, such as a water-methanol or water-acetonitrile solvent system that contains 1.0 to 2.0 equivalents of acetic acid. As a result, the mono- and bis salts of sulcardine are formed. See Streitwiesser et al., INTRODUCTION TO ORGANIC CHEMISTRY 4$^{th}$ ed. (Macmillan Publishing Co.), at page 736.

2. Reaction of Sulcardine with an Alkyl Halide

In generally, quaternary ammonium halides can be prepared by reacting an alkyl or an araalkyl halide with an appropriate tertiary amine in a non-reactive organic solvent. By the same token, sulcardine could be reacted with an alkyl bromide or alkyl iodide in ether or tetrahydrofuran, at room temperature, to form corresponding methyl salts via the formation of a methylpyrrolidinium cation. The stoichiometry of alkyl halide in the reaction would dictate the type of salt formed. Thus, adding 1.0 mole of an alkyl halide would give the mono corresponding pyrrolidinyl methyl salt, while the addition of 2.0 moles of an alkyl halide would allow for the formation of the bis salt. See Streitwiesser et al., supra, at page 737.

3. Formation of Alkali Metal Salts of Sulcardine

Synthesis of alkali metal salts of sulcardine entails use of a strong base to effect abstraction of the —NH proton of sulfonamide. Accordingly, the addition of sodium hydride to a cold, rapidly stirring solution of sulcardine in an aprotic anhydrous solvent, such as anhydrous tetrahydrofuran, should result in the formation of a sodium salt as represented in Formula I:

See Singh et al., BIOORGANIC & MED. CHEM. LETTERS 16: 3921-26 (2006).

The reaction would be carried out by the drop-wise addition of a tetrahydrofuran solution of sodium hydride to a cold, round-bottom flask, which contains a solution of sucradine. After completing the addition of the sodium hydride, the reaction would be warmed to room temperature and stirred. The reaction would be complete when no more hydrogen gas is evolved.

In some embodiments, the composition administered to the subject further comprises a pharmaceutically acceptable excipient or carrier or other agent. The amount of the active agent in the composition can vary within the full range employed by those skilled in the art. Typically, the composition will contain, on a weight percent (wt %) basis, from about 0.01-99.99 wt % of the active agent based on the total formulation, with the balance being one or more suitable pharmaceutical excipients. Preferably, the active agent is present at a level of about 1-80 wt %.

Pharmaceutically acceptable excipients suitable for carrying out the invention include, without limitation, buffers, diluents, tonicity agents, stabilizers, antioxidants, preservatives and mixtures thereof. Examples of suitable pharmaceutically acceptable excipients are disclosed herein.

In some embodiments, the pharmaceutically acceptable excipient is a buffer. In one aspect, the buffer is a glycine buffer. In another aspect, the buffer is a histidine buffer. The concentration of the buffer, in one aspect, is between about 1 mM and about 100 mM, or alternatively about 2 mM to about 40 mM, or alternatively about 5 mM to about 20 mM. In another aspect, the concentration of the buffer is about 10 mM. The pH of the buffer can be independently adjusted. In one aspect, the pH of the buffer is from about 2 to about 9, or alternatively from about 2.5 to about 7, or alternatively from about 3 to about 5 or alternatively about 3.

In some embodiments, the pharmaceutically acceptable excipient is a diluent. In one aspect, the diluent is saline. In another aspect, the diluent is 5% dextrose.

In further some embodiments, the pharmaceutically acceptable excipient is a stabilizer. In one aspect, the stabilizer is selected from the group consisting of sorbitol, EDTA and glycerol. In another aspect, the stabilizer is sorbitol present at about 3% concentration in the composition. In yet another aspect, the stabilizer is EDTA present at about 0.05% concentration in the composition. In further another aspect, the stabilizer is glycerol present at about 2% concentration in the composition.

The effective amount of the active agent or the composition administered can be experimentally determined and can vary depending upon the specific agent, the disease or symptom to be treated or alleviated, the age, gender and weight of the subject to be treated, the dosing regimen of the formulation, the severity of the disease condition, the manner of administration and the like, all of which can be determined readily by one of skill in the art.

Administration of the active agent or the composition can be made by methods known in the art. In one aspect, the route of administration is intramuscular injection. In another aspect, the route of administration is intravenous injection. In another aspect, the route of administration is subcutaneous injection. In further another aspect, the route of administration is oral, rectal, buccal, intravaginal, sublingual, transdermal, inhalation or nasal administration. It will also be appreciated that the preferred route will vary with the condition and age of the recipient, and the disease being treated. Intravenous administration represents a preferred means for achieving rapid and consistent blood levels of drug, avoiding the variables associated with oral, nasal, buccal, subligual, transdermal or rectal administration or other means for being a preferred route of administration for acute or paroxysmal AF with the intent to cardiovert. In the treatment of recurrent AF, where daily administrations for prolonged periods, if not indefinitely, are common, parenteral administration methods are less desirable. Oral or transdermal administration routes are more preferred allowing for controlled and sustained absorption of drug into the blood stream over time when specific controlled release formulations are use. These routes of administration also represent the most desirable from a patient compliance perspective. Methods of determining the most effective means and dosage of administration are known to those of skill in the art and will vary with the composition used for therapy, the purpose of the therapy, and the subject being treated. Single or multiple administrations can be carried out with the dose level and pattern being selected by the treating physician. Suitable dosage formulations and methods of administering the agents are known in the art.

Administration of the active agent or the composition can be composed of one dose, or a number of consecutive doses. Multiple doses can be comprised of similar doses or an initial larger loading dose followed by smaller multiple maintenance doses or controlled release/delivery. The amount and frequency of dosage can be determined with methods known in the art, and will vary depending on factors such as the risk of continued risk, half life of the active ingredient and toxicity of the active agent or the composition.

Administration of the formulation of the invention can be made at one site of the subject, or multiple sites of the subject. The amount of dosage and sites can be determined with methods known in the art. In one aspect, the administration is one or more intravenous injection at the thigh or the arm of the subject. In another aspect, the administration is one or more intramuscular injection at the rear thigh of the subject.

The subject suitably treated by the methods and formulation of the invention can be a mammal including a human. Non-human animals subject to treatment include, for example, a simian, a murine, a canine, a leporid, such as a rabbit, livestock, sport animals, and pets.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

Example 1

Inhibitory Concentration at Half Maximal Inhibition (IC50) in Atrial Cardiomyocytes Isolated from Various Species The IC50 values obtained from rabbit and human atria (Table 1), as well as disclosures made previously, suggest that target blood concentrations or cardiac tissue concentrations need to be in the range of 26 µM to 100 µM to achieve meaningful ion channel blockade of fast and slow Na, L-type Ca, Ikr and Ito channels in atrial tissue and hence elicit an atrial antiarrhythmic effect.

TABLE 1

Rabbit and Human Atrial Cardiomyocyte IC50's

| Species/Cardiac Origin | Ion Channel Profiling (IC50, µM) in isolated atrial cardiomyocytes | | | | | | |
|---|---|---|---|---|---|---|---|
| | Fast Na | L-Ca | Ito | IKr | IKach | Slow Na | IKur |
| Rabbit/atria | 34 | 54 | 26 | 61 | 130 | — | — |
| Human/atria | 26 | 40 | 100 | 40 | — | 45 | >190 |

Example 2

Cardiovascular Safety Effects of Various Dose Levels of Sulcardine Sulfate in Dogs and Blood Levels Achieved Dogs were administered morphine (2 mg/kg subcutaneously) approximately 10-19 minutes prior to administration of anesthesia. Dogs were anesthetized with 1% α-chloralose (100 mg/kg intravenous), followed by a constant infusion of α-chloralose (35-75 mg/kg/hr, IV). Two healthy female dogs were administered escalating doses of sulcardine sulfate intravenously over 15 minutes in an acetate buffer system at dose levels of 10, 30 and 90-mg/kg with dose administrations separated by 60 minutes. Following drug administration, dogs were evaluated for ventricular, pulmonary and peripheral hemodynamic changes using Swanz Ganz and femoral catheters as well as by monitoring of blood oxygen saturation, test article blood level, body temperature, blood biochemistries, hematologies, ECG, and histamine.

Hemodynamic Results

Hemodynamic effects were observed with all doses of sulcardine sulfate. During the initial infusion of sulcardine sulfate in dogs 10 mg/kg, the changes included marked increases in heart rate (HR) (+194% to +271%) and contractility (+96% to +109%). Left ventricular end diastolic pressure (LVEDP) displayed an initial increase immediately post dosing followed by a pronounced decrease (−157% to −710%). Mean pulmonary arterial pressure (MPAP) (+35% to +76%) and cardiac output (CO) (+80 to 131%) were also increased after sulcardine sulfate administration at 10 mg/kg. During the same period, an initial increase (+66%) in mean arterial pressure was observed in one animal out of two which attained its maximum at 10 minutes post start of dosing. However, both animals eventually displayed a decreased in mean arterial pressure (MAP) in the post-dose period (−33% to −41%). Maximal effects were observed at approximately 10 minutes into the infusion and returned gradually toward baseline at the end of the 60 minutes monitoring period with the exception of HR, contractility and LVEDP which remained elevated throughout the monitoring period. Similar hemodynamic changes were observed with the initiation of the second infusion (30 mg/kg) with the exception of HR and contractility which slightly decreased during dosing up to the end of the infusion followed by an increase after dosing was completed. At 90 mg/kg, all animals succumbed at the completion of the final 15-minute infusion where cardiac depression leading to severe hypotension was present.

Histamine Profiling

Histamine analysis results indicate normal histamine levels during pre-treatment in all animals. Following test article administration, increases in histamine levels were observed in both groups and at all dose levels. A severe increase in histamine plasma concentration at 10 mg/kg sulcardine sulfate reaching maximums of 1874 nM and 1919 nM at 5 min and 10 min post-Rx respectively versus pretreatment values of 9.48 and 14.341 respectively and gradually decreased, although remaining elevated over the 60 minute observation period compared to baseline values. Subsequent doses of sulcardine sulfate resulted in increases that were milder in amplitude as the dose increased with maximums that peaked during dosing or at 10 min post administration. Maximum levels of plasma concentration of 251 nM and 183 nM were observed at 30 mg/kg while maximums of only 99 nM and 64 nM were observed at 90 mg/kg. This reaction is possibly due to a mastocyte granule depletion following the preliminary exposure to test article.

Changes in hemodynamics after dosing with sulcardine sulfate were in part attributable to release of histamine after dosing, although only in part as pretreatment with an antihistamine (diphenhydramine) only partially corrected these hemodynamic effects (data not shown).

Electrocardiography

A dose dependant increase in QTc was observed in all animals. Slight QTc prolongations were noted (up to approximately 20 msec) within 5 minutes of the initiation of treatment with sulcardine sulfate at 10 mg/kg. Cumulative dose-dependent prolongations of QTc intervals were seen at the initiation of the 30 mg/kg infusion (approximately 35 msec) which became more pronounced at 90 mg/kg (ranging from approximately 50 to 120 msec increase from baseline QTc values). QRS widening was also noted at all dose levels, with evidence of dose-response.

Pharmacokinetic Results

The mean peak sulcardine sulfate concentrations which peaked generally at the minutes post initiation time point of each 15 minute infusion of sulcardine sulfate at 10, 30 and 90 mg/kg were 1.8, 11.2 and 100.1 µg/mL respectively which translated into approximately 4, 24.6 and 218 µM.

Conclusions

At a dose of sulcardine sulfate (30 mg/kg) which achieved peak plasma concentrations (25 µM) approaching the low end range of patch clamp IC50 values in human atrial cardiomyocytes for Na, L-Ca and Ikr channels, significant drops in mean arterial pressure, tachycardia, QT interval prolongation and changes in ventricular contractility were observed. Atrial patch clamp and dog cardiovascular safety and PK findings suggest that it may not be possible to achieve plasma levels suggested by patch clamp as being in the pharmacologic range for antiarrhythmic effects on atrial fibrillation using sulcardine sulfate administered by relatively short term drug infusion periods (≦15 minutes) without experiencing significant untoward effects on hemodynamics and ECG.

Example 3

Sulcardine Sulfate Pharmacokinetic Parameters

Figure 1:
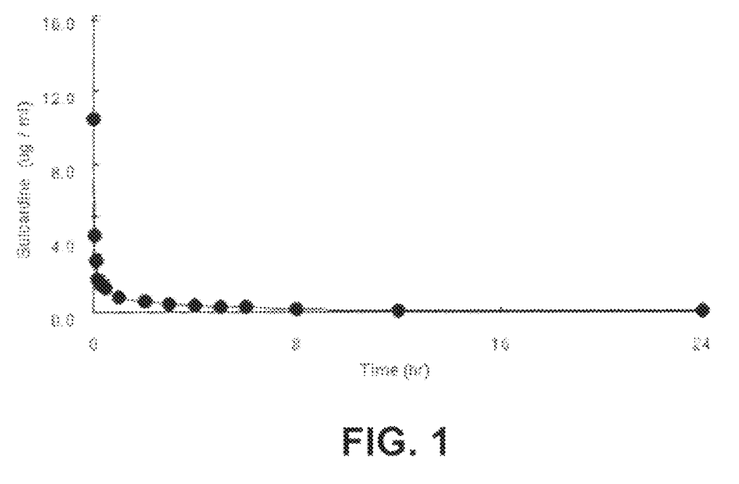
FIG. 1 presents the pharmacokinetics (PK) curve of sulcardine sulfate after fast IV infusion. The total amount of sulcardine sulfate injected was 8 mg/kg.

In dogs an PO dose of 40 mg/kg (efficacious oral dose range) gives peak levels of 2.1 µg/mL (4.6 µM). IV data at 8 mg/kg (efficacious range) did not provide a Cmax (Table 2, FIG. 1), but from the curve below the table it can be seen that the Cmax appears to be about 10 µg/mL following IV administration of an efficacious dose against ventricular arrhythmia. With a 60 minute infusion, as envisioned for the planned AF dog efficacy study and as further contemplated to be a clinical route of administration, this Cmax value will be reduced appreciably, perhaps to under 5 µg/mL (11 µM). These PK data and extrapolated conclusion are in agreement with the CV safety study, where PK after 15 minute infusion was conducted. In general, the mean concentrations peaked at the 10-minute time point, post-initiation, for each 15-minute infusion of sulcardine sulfate at 10 and 30 mg/kg (efficacious dose against ventricular arrhythmia). The mean peak plasma concentrations were 1.8 (4.2 µM) and 11.2 µg/mL (24.6 µM), respectively (data not shown). These values were well below in the case of the lower dose to barely reaching some but not all atrial cell patch clamp IC50s on various ion channels, although still associated with significant drops in mean arterial pressure, tachycardia, QT interval prolongation and changes in ventricular contractility were observed.

TABLE 2

Plasma PK parameters of sulcardine sulfate in Beagle dog after oral and IV administration

| PK Parameter | 40 mg·kg⁻¹(po) Mean ± SD | 80 mg·kg⁻¹(po) Mean ± SD | 160 mg·kg⁻¹(po) Mean ± SD | 8 mg·kg⁻¹ (fast i.v push) Mean ± SD |
|---|---|---|---|---|
| V/F (c) | 12.08 ± 2.621 | 16.60 ± 18.60 | 6.528 ± 0.6551 | 2.815 ± 1.714 |
| $T_{1/2\alpha}$(hr) | 1.636 ± 0.6148 | 1.670 ± 1.068 | 1.758 ± 1.790 | 0.2898 ± 0.2041 |
| $T_{1/2\beta}$(hr) | 12.21 ± 3.412 | 8.631 ± 2.294 | 9.640 ± 1.532 | 6.107 ± 1.537 |
| $T_{1/2Ka}$(hr) | 0.5663 ± 0.1687 | 0.3681 ± 0.2443 | 0.8257 ± 0.5284 | / |
| $K_{21}$(hr⁻¹) | 0.1778 ± 0.1295 | 10.10 ± 19.85 | 1.474 ± 1.562 | 0.5196 ± 0.3149 |
| $K_{10}$(hr⁻¹) | 0.1748 ± 0.0306 | 0.1166 ± 0.0731 | 0.0856 ± 0.0155 | 0.7378 ± 0.2645 |
| $K_{12}$(hr⁻¹) | 0.1806 ± 0.0817 | −8.226 ± 16.60 | −0.0620 ± 0.1371 | 1.982 ± 1.157 |
| AUC | 19.57 ± 2.414 | 83.53 ± 21.27 | 291.6 ± 29.13 | 4.750 ± 1.778 |
| $CL_s$ | 2.065 ± 0.2283 | 1.013 ± 0.2956 | 0.5527 ± 0.0533 | 1.850 ± 0.5911 |
| $T_{max}$ | 1.508 ± 0.4160 | 1.407 ± 0.6461 | 2.700 ± 1.001 | / |
| $C_{max}$ | 2.121 ± 0.4025 | 8.849 ± 1.789 | 19.10 ± 3.412 | / |

Example 4

Cardiovascular Safety Effects of Various Dose Levels of Sulcardine Sulfate in Primates and Blood Levels Achieved Female Cynomolgus monkeys were administered morphine (2 mg/kg subcutaneously) prior to induction of anesthesia. Monkeys were anesthetized with 1% α-chloralose (100 mg/kg intravenous), followed by a constant infusion of α-chloralose 40 mg/kg/hr, IV which was reduced to 30 mg/kg/hr approximately 92 to 98 min pre treatment due to low blood pressure. Monkeys were placed on a heating pad set to maintain the animal's body temperature at approximately 37° C. Body temperature was monitored throughout the experiment via a rectal thermometer or via the Swan Ganz (thermodilution catheter) once implanted. Monkeys were intubated and placed on a ventilator supplemented with oxygen to maintain oxygenation within the normal physiological range. The animals were mechanically ventilated at a rate of 12 breaths/minute and a pressure of 17-18 cm $H_2O$. The following parameters were regularly monitored in order to ensure proper ventilation of the animals but are not reported: $SpO_2$, inspiratory and expiratory $CO_2$, inspiratory $O_2$ and respiratory rate.

A Swan Ganz (thermodilution catheter) was inserted into the right femoral vein via phlebotomy and advanced into the pulmonary artery for cardiac output measurements. A catheter was inserted in the left femoral artery via an arteriotomy for blood gas determination. Another catheter was inserted in the left femoral vein for blood collection for toxicokinetic evaluation. Finally, an incision was also performed on the left side of the neck to expose the left carotid artery and an electronic dual pressure sensor catheter (Millar) was placed via arteriotomy and advanced into the left ventricle. The catheter was positioned to simultaneously collect left ventricle blood pressure measurements as well as aortic pressure. In addition, a temporary catheter was placed in any of the cephalic veins for administration of Lactated Ringers at 10 mL/kg/hr throughout the course of the experiment.

Following surgical preparation, hemodynamic and electrocardiographic parameters were allowed to stabilize for at least 15 minutes. The vehicle control and test article were then administered, and hemodynamic, electrocardiographic parameters were monitored. Histamine and plasma PK data was obtained.

Hemodynamic Results

Sulcardine sulfate administration produced dose related cardiovascular changes. At 10 mg/kg, the changes observed included an increase in mean pulmonary arterial pressure (+25% to 69%), combined with a relatively stable heart rate (HR) (within 10%) and decreased contractility (−48% to −55%). Most of these effects were observed immediately post initiation of test article administration and peaked at its completion. All parameters returned toward normal values before the next dose.

The second dose of sulcardine sulfate at 30 mg/kg induced changes similar to the first dose with the addition of a drop in mean arterial pressure (up to −69%) and decreases in mean pulmonary arterial pressure (−31% to −88%). Contractility (−69% to −77%) and heart rate (−24% to −54%) also decreased during the same period. Again, at the completion of infusion, heart rate returned toward baseline while contractility remained moderately decreased (−28% to −25%). Mean arterial pressure increased (+32% to 43%). Mean pulmonary arterial pressure increased in a pronounced fashion (up to +245%) and remained considerably elevated in one animal out of two.

Infusion of sulcardine sulfate at 90 mg/kg was associated with severe hypotension and hypocontractility leading to death in both animals before completion of the 15-minute infusion.

Electrocardiography

A dose dependant increase in QTcB was observed in both animals. Slight QTcB prolongation was noted (19 to 20 msec) in both animals peaking at 2 minutes post-treatment with sulcardine sulfate at 10 mg/kg. Cumulative dose-dependent prolongations of QTcB intervals were seen in both animals at the initiation of the 30 mg/kg infusion (60 to 123 msec) reaching a maximum at 5 minutes post-completion of infusion. The QTcB prolongation became more pronounced at 90 mg/kg (reaching 78 and 112 msec increase from baseline QTcB values).

QRS widening was also noted at all dose levels, with evidence of dose-response. At 10 mg/kg sulcardine sulfate resulted in an increase of QRS of 11% and 26% from baseline. Further prolongation of QRS was noted at 30 mg/kg with a maximum increase ranging between 59% and 119% from baseline. QRS interval recorded during infusion at 90 mg/kg presented the most important changes noted with 88% and 133% increase from baseline. Dose dependant QRS widening is an expected pharmacological observation for a multi-channel blocker.

A dose-dependant PR interval increase also was observed in both animals, with prolongation first noted at 10 mg/kg in both animals (+18% and +30%). Further increases were noted at 30 and 90 mg/kg. One animal (1602B) presented a sinoatrial block with a ventricular escape rhythm shortly before death. All these observations are compatible with exaggerated pharmacological activity of a multi-ion channel blocker.

One animal (1501A) presented right bundle branch block (RBBB) during infusion at 30 mg/kg. Animal 1602B also presented a RBBB during infusion of 90 mg/kg. Right bundle branch block is a common observation in monkeys which is likely to result from reduction of conduction. Similar electrocardiographic changes have been reported with other antiarrhythmic drugs (e.g., disopyramide) and may be associated with exaggerated pharmacologic properties of sulcardine sulfate.

Histamine Profiling

Blood samples for histamine levels determination samples were collected without any notable deviations from the targeted collection time points.

There were no appreciable increases in histamine levels following test article administration at 10 mg/kg. Animal No. 1501A did show transient increases after 10 minutes of the 30 mg/kg infusion and then increasing again after initiation of the 90 mg/kg infusion and at time of death. No appreciable increases were observed in Animal No. 1602B at any dose levels.

Pharmacokinetic Results

The mean plasma concentrations of sulcardine sulfate which peaked generally at 10 minutes post initiation of each 15 minute infusion at 10, 30 and 90 mg/kg were 9.8, 74.3 and 845.5 ug/mL respectively, which were equivalent to 21.6, 163.5 and 1,860.1 µM.

Conclusions

Using an infusion protocol of ≦15 minutes, a dose of 10 mg/kg of sulcardine sulfate, which generated peak plasma concentrations (23 µM) in the low end of the target range suggested as possible efficacious against atrial arrhythmias as illustrated by atrial patch clamp IC50s (26-100 µM), resulted in some alterations in hemodynamics including a decrease in ventricular developed pressure and an increase in pulmonary aterial pressure. A tripling of that dose to 30 mg/kg resulted in peak plasma levels of 163 µM, now slightly above the minimal target concentration required to inhibit all atrial ion channels the drug is active upon. At this dose, rate of administration and plasma concentration, a significant drop in mean arterial pressure (67%) and further decreased in ventricular contractility. Modest prolongation of QT interval, QRS and RP intervals was observed at a 21 µM plasma level, and became quite consequential at a plasma concentration of 164 µM. Consequently the effects of sulcardine sulfate to reduce blood pressure, contractility and to extend QT interval are seen at plasma concentrations predicted to be at the low end of the therapeutic range for treating atrial arrhythmias based upon human atrial patch clamp data. The data suggests it may not be possible to achieve blood concentrations of sulcardine sulfate that are effective on atrial arrhythmias without experiencing untoward effects on hemodynamics, QT interval. Effects of the drug on hemodynamics appear to be completely unrelated to histamine release in primates, in comparison with dogs where some degree of the hemodynamic effects, especially effects on heart rate may be a result of histamine release.

Example 5

Cardiovascular Safety Effects of Various Dose Levels of Sulcardine Sulfate in Minipigs and Blood Levels Achieved Animals were administered morphine (2 mg/kg subcutaneously) prior to induction of anesthesia. Animals were anesthetized with 1% α-chloralose (100 mg/kg intravenous bolus), followed by a constant infusion of α-chloralose which was gradually increased from 20 mg/kg/hr to attain a definitive rate between 30 and 40 mg/kg/hr, IV before administration of the test article. Animals were placed on a heating pad set to maintain the animal's body temperature at approximately 37° C. Body temperature was monitored throughout the experiment via a rectal thermometer or via the Swan Ganz (thermodilution catheter) once implanted. Animals were intubated and placed on a ventilator supplemented with oxygen to maintain oxygenation within the normal physiological range. The animals were mechanically ventilated at a rate of 11-13 breaths/minute and a peak inspiratory pressure of 18 cm $H_2O$. The following parameters were regularly monitored in order to ensure proper ventilation of the animals but are not reported: $SpO_2$, inspiratory and expiratory $CO_2$, inspiratory $O_2$ and respiratory rate.

A Swan Ganz (thermodilution catheter) was inserted into the right femoral vein via phlebotomy and advanced into the pulmonary artery for cardiac output measurements. A catheter was inserted in the left femoral artery via an arteriotomy for blood gas determination. Another catheter was inserted in the left femoral vein for blood collection for toxicokinetic evaluation. Finally, an incision was also performed on the left side of the neck to expose the left carotid artery and an electronic dual pressure sensor catheter (Millar) was placed via arteriotomy and advanced into the left ventricle. The catheter was positioned to simultaneously collect left ventricle blood pressure measurements as well as aortic pressure. In addition, a temporary catheter was placed in any of the cephalic veins for administration of Lactated Ringers at 10 mL/kg/hr throughout the course of the experiment.

Following surgical preparation, hemodynamic and electrocardiographic parameters were allowed to stabilize for at least 15 minutes. The vehicle control and test article were then administered, and hemodynamic, electrocardiographic, histamine and PK parameters were monitored.

Hemodynamic Results

Sulcardine sulfate administration produced dose-related changes. At 10 mg/kg, the changes observed included a decrease in contractility (−51% to −52%), a decrease in pulse pressure (−26% to −37%) combined with a slight increase in heart rate (+19% to 27%). Cardiac output was also reduced (−13% to −16%) during the same period. Most of these effects were observed immediately post initiation of test article administration and peaked at its completion. Partial recovery was noted for all parameters before the next dose.

The second dose of sulcardine sulfate (30 mg/kg) induced changes similar to the first dose, but of a greater magnitude. Decrease in contractility (−76% to −78%), pulse pressure (−56 to −59%) and systemic arterial pressures (systolic, mean and diastolic) were noted in both animals. These changes were combined with a decrease in cardiac output (−45% to −49%) and increased heart rate (+40% to 41%) which was considered a compensatory response to systemic hypotension. Arterial pressure and cardiac output returned toward normal levels by the end of the 60 minutes monitoring period following the second dose but heart rate. Changes in pulmonary arterial pressure (PAP), pulmonary vascular resistance (PVR) and systemic vascular resistance (SRV) were considered secondary to decreased contractility and cardiac output.

Infusion of sulcardine sulfate at 90 mg/kg was associated to cardiac depression with severe hypotension and hypocontractility leading to death as both animals succumbed during or at completion of the 15-minute infusion.

Histamine Profiling

Histamine analysis results indicate normal histamine levels during pre-treatment for both animals. There were no appreciable increases in histamine levels following test article administration at all doses.

Electrocardiography

A dose dependent effect on atrioventricular conduction such as increased QRS complex duration, HR and QTcC interval were observed in one or both animals starting at 10 mg/kg dose. Animal 1601C displayed a 15% QTcC prolongation at 10 mg/kg followed by increasing effects in both animals at 30 and 90 mg/kg (up to 30%). A dose dependant PR interval increase was also noted in both animals with prolongation first noted at 10 mg/kg in both animals (+38% and +10%). Further increases were again noted at 30 and 90 mg/kg. A similar dose dependent pattern of increasing QRS durations were noted in both animals starting at 10 mg/kg. All these observations are compatible with exaggerated pharmacological activity of a multi-ion channel blocker.

Pharmacokinetic Results

Peak plasma concentrations of sulcardine sulfate increased with increasing dose. The mean concentrations which peaked generally at the 10 minutes post initiation time point of each 15 minute infusion of sulcardine sulfate at 10, 30 and 90 mg/kg were 6.20, 19.9 and 25.6 ug/mL respectively, which translated into a plasma concentration of 13.6, 43.8 and 56.3 μM.

treating atrial arrhythmias based upon human atrial patch clamp data. The data suggests it may not be possible to achieve blood concentrations of sulcardine sulfate that are effective on atrial arrhythmias without experiencing untoward effects on hemodynamics and QT interval. Effects of the drug on hemodynamics appear to be completely unrelated to histamine release in minipigs, in comparison with dogs where some degree of the hemodynamic effects, especially effects on heart rate may be a result of histamine release.

Example 6

Administration Rate-Dependent Hemodynamic Effects

The effect of sulcardine sulfate intravenously administered over a 10 minute infusion on the mean blood pressure, heart rate, and plasma histamine concentration of conscious beagle dogs was performed. Three male and female purpose-bred beagles, weighing 10.0-12.7 Kg were intravenously administered repeated increasing doses of sulcardine sulfate (cumulative dose 1-44 mg/kg) at 15 minute intervals following a 10 minute infusion of the prior dose. The administered doses were as follows: 1 mg/kg, 3 mg/kg, 10 mg/kg, and 30 mg/kg sulcardine sulfate. Heart rate, mean arterial blood pressure, and histamine concentrations were measured (Table 3) at 10 minute intervals after completion of each drug infusion period.

TABLE 3

Data Summary of Sulcardine Sulfate on Hemodynamics Following Delivery by 10 Minute Infusion

| | | Sulcardine Sulfate Dose | | | |
|---|---|---|---|---|---|
| | Pretreatment | 1 mg/kg | 3 mg/kg | 10 mg/kg | 30 mg/kg |
| Heart rate (bpm) | 80.00 ± 7.64 | 90.00 ± 12.58 | 110.00 ± 10.41 | 111.7 ± 17.64 | 111.7 + 6.01 |
| Mean blood pressure (mmHg) | 167.7 ± 10.97 | 166.7 ± 10.99 | 170.7 ± 7.36 | 101.0 ± 28.45 | 69.7 ± 14.7* |
| Histamine Concentration (ng/mL) | 86.64 ± 10.63 | 93.95 ± 24.11 | 182.5 ± 46.11 | 252.6 ± 85.78 | 465.9 ± 27.75* |

Conclusions

A dose of 10 mg/kg of sulcardine sulfate, administered over 15 minutes, which generated peak plasma concentrations (13.6 μM), a concentration below the target range suggested as possible efficacious against atrial arrhythmias as illustrated by patch clamp IC50s (26-100 μM), resulted in appreciable drops in blood pressure, contractility and cardiac output and a compensatory tachycardia. A tripling of that dose to 30 mg/kg resulted in peak plasma levels of ~44 μM, now within the minimal target concentration range required to inhibit some, but not all the atrial ion channels the drug is active on. At this dose and plasma concentration, a further drop in arterial pressure, ventricular contractility and cardiac output occurred and tachycardia worsened. Modest prolongation of QT interval, QRS and RP intervals was observed at a 13.6 μM plasma level, and became more pronounced at higher plasma concentrations. Consequently the effects of sulcardine sulfate to reduce blood pressure, contractility, cardiac output and to extend QT interval are seen at plasma concentrations predicted to be below the therapeutic range for During the course of the study it was observed that the intravenous administration of sulcardine sulfate over 10 minutes was associated with a dose-dependent decrease in arterial blood pressure that was accompanied by the appearance of an erythemitous flare in the region of the face and ears plus the appearance of urticaria (hives). The effect became less intense with successive injections, most likely due to the depletion of mast cell stores of histamine. A dose dependent increase in plasma histamine concentrations was documented by an ELISA assay.

Three additional animals received sulcardine sulfate (14 mg/kg, i.v.) infused over 45 minutes. The purpose of this study was to investigate whether or not a slow infusion (45 min) of sulcardine sulfate would affect heart rate and blood pressure. The results are summarized in Table 4. The data show a progressive increase in the resting heart rate during infusion. The change in blood pressure was modest, most likely due to a compensatory increase in the resting heart rate. Thus, the slow intravenous administration of sulcardine sulfate in a total intravenous dose of 14 mg/kg did not result in a marked change in resting blood pressure and/or heart rate as observed with bolus injection.

TABLE 4

Effects of Sulcardine Sulfate (14 mg/kg) on Heart Rate and Blood Pressure over 45 minutes of Infusion

| | Time (minutes) | | | | |
|---|---|---|---|---|---|
| | 0 | 10 | 25 | 40 | 55 |
| Heart rate (bpm) | 73.3 ± 3.3 | 95.0 ± 7.6 | 115.0 ± 5.8* | 115.0 ± 5.0* | 103.3 ± 6.0 |
| Mean blood pressure (mmHg) | 168.7 ± 5.2 | 165.3 ± 0.3 | 167.7 ± 9.8 | 162.7 ± 11.3 | 152.0 ± 16.2 |

N = 3;
*P < 0.05 vs. 0 Minutes, Repeated Measures ANOVA

A hemodynamic effects study of sulcardine sulfate in an anesthetized post-MI sudden cardiac death model study was also performed. The study population consisted of ten purpose-bred, female beagle dogs, weighing 10.0-12.0 Kg. The animals had left ventricular wall ischemic injury induced by a 90-minute occlusion of the left anterior descending coronary artery followed by reperfusion. Five animals were treated with sulcardine sulfate (15 mg/kg) infused intravenously over 10 minutes, and the remaining five animals were vehicle dogs treated with 0.9% sodium chloride solution (placebo). Lowest mean arterial blood pressure was measured every 15 minutes for a total period of 120 minutes after treatment. The results are summarized in FIG. 2.

Figure 2:
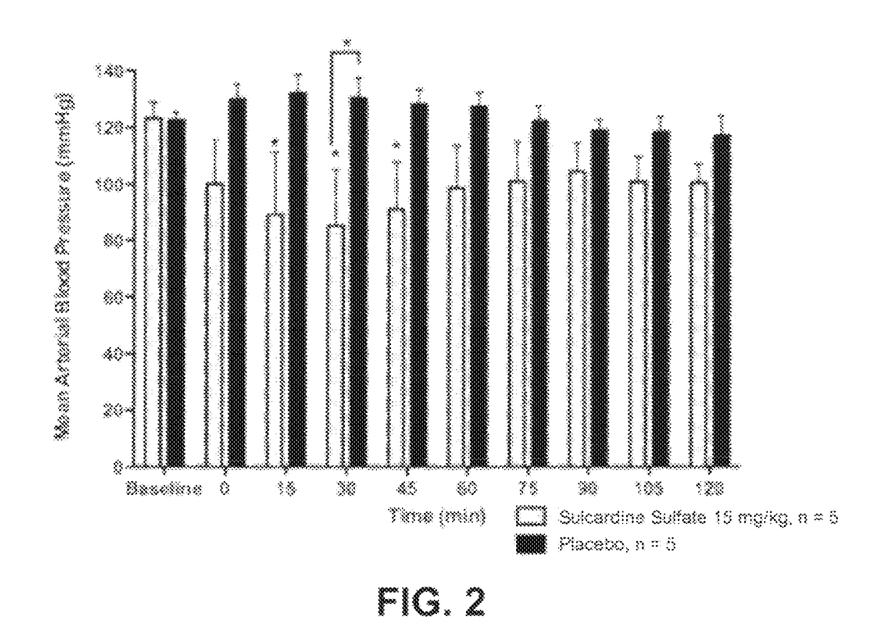
FIG. 2 shows hemodynamic effects of a 45 minute intravenous sulcardine sulfate infusion administered to anesthetized dogs in the sudden death model. Time on X axis represents time after completion of the 45 minute drug infusion.

The mean arterial blood pressures at fifteen, thirty, and forty-five minutes after completing a 10 minute infusion of sulcardine sulfate (15 mg/kg) were significantly lower compared to sulcardine sulfate baseline values (P<0.05, Repeated Measures ANOVA). The mean arterial blood pressure in vehicle animals did not change significantly over time. P<0.05 Placebo vs sulcardine sulfate using Two Way ANOVA. Upon completion of the min sulcardine sulfate infusion, there was a gradual and progressive return of the arterial blood pressure that was not different from pre-drug baseline or the placebo treated animals by 50 minutes following completion of drug infusion.

Example 7

Hemodynamic Effects of Short Term Infusion of Sulcardine Sulfate when Combined with Diphenhydramine Pretreatment in Anesthetized Dogs Dogs were administered morphine (2 mg/kg subcutaneously) approximately 10-19 minutes prior to administration of anesthesia. Dogs were anesthetized with 1% α-chloralose (100 mg/kg intravenous), followed by a constant infusion of α-chloralose (35-75 mg/kg/hr, IV). Two healthy female dogs were administered escalating doses of sulcardine sulfate intravenously over 15 minutes in an acetate buffer system at dose levels of 10, 30 and 90 mg/kg with dose administrations separated by 60 minutes. Another set of two dogs received test article after pre-treatment with diphenhydramine (1 mg/kg administered 30 minutes prior to start of test article infusion). Following drug administration, dogs were evaluated for ventricular, pulmonary and peripheral hemodynamic changes using Swanz Ganz and femoral catheters as well as by monitoring of blood oxygen saturation, test article blood level, body temperature, blood biochemistry, hematology, ECG, and histamine levels.

Hemodynamic Results

Group 1 (Sulcardine sulfate at 10, 30 and 90 mg/kg). Hemodynamic effects were observed with all doses of sulcardine sulfate. During the initial infusion of sulcardine sulfate in dogs not pre-treated with diphenhydramine at 10 mg/kg, the changes included marked increases in heart rate (HR) (+194% to +271%) and contractility (+96% to +109%). Left ventricular end diastolic pressure (LVEDP) displayed an initial increase immediately post dosing followed by a pronounced decrease (−157% to −710%). Mean pulmonary arterial pressure (MPAP) (+35% to +76%) and cardiac output (CO) (+80 to 131%) were also increased after sulcardine sulfate administration at 10 mg/kg. During the same period, an initial increase (+66%) in mean arterial pressure was observed in one animal out of two which attained its maximum at 10 minutes post start of dosing. However, both animals eventually displayed a decreased in mean arterial pressure (MAP) in the post-dose period (−33% to −41%). Maximal effects were observed at approximately 10 minutes into the infusion and returned gradually toward baseline at the end of the 60 minutes monitoring period with the exception of HR, contractility and LVEDP which remained elevated throughout the monitoring period. Similar hemodynamic changes were observed with the initiation of the second infusion (30 mg/kg) with the exception of HR and contractility which slightly decreased during dosing up to the end of the infusion followed by an increase after dosing was completed. At 90 mg/kg, all animals succumbed at the completion of the final 15-minute infusion where cardiac depression leading to severe hypotension was present.

Group 2 Animals: Sulcardine sulfate at 10, 30 and 90 mg/kg with diphenhydramine (1 mg/kg) administered approximately 30 minutes before treatment with 10 mg/kg sulcardine sulfate. Animals pre-treated with diphenhydramine (H1 antagonist) and dosed with sulcardine sulfate at 10 mg/kg, presented hemodynamic changes which are mediated by H2 receptors. The changes resembled those noted in Group 1 animals, but were of a reduced magnitude. Changes included marked increases of heart rate (HR) (+124% to +157%) however not sustained, and contractility (+41% to +58%), mean pulmonary arterial pressure (MPAP) (+30% to +57%) and Cardiac output (CO) (+108 to 184%) with a slight decreased mean arterial pressure MAP (−12% to −17%). Left ventricular end diastolic pressure (LVEDP) which displayed an initial increase immediately post dosing followed by a severe decrease (−163% to −435%). Maximal effects were observed at approximately 10-15 minutes into the infusion and returned gradually toward baseline at the end of the 60 minutes monitoring period with the exception of MAP of one animal out of two where the decrease was sustained. Increased contractility and decreased LVEDP were noted throughout the monitoring period. Similar hemodynamic changes were observed with the initiation of the second infusion (30 mg/kg) with the exception of HR and contractility which presented a second increase (+158 to +174% and +25% to +33% respectively). These cardiovascular changes correlate with plasma histamine levels. The severity of tachycardia increased above 200% of baseline after completion of dosing at 30 mg/kg. At 90 mg/kg, as for the Group 1 animals, all animals succumbed at the completion of the final 15-minute infusion as progressive and severe hypotension was noted.

While the invention has been described in conjunction with the above embodiments, the foregoing description and examples are intended to illustrate and not to limit the scope of the invention. Other aspects, advantages and modifications within the scope of the invention will be apparent to those skilled in the art to which the invention pertains.

What is claimed is:

1. A method of treating atrial fibrillation (AF), comprising administering to a subject who suffers from or is at risk of suffering from AF a composition comprised of an amount of an active agent that is 4-methoxy-N-(3,5-bis-(1-pyrrolidinyl)-4-hydroxy benzyl)benzene sulfonamide or a pharmaceutically acceptable salt thereof, such that the maximum steady state plasma concentration (Cmax) of said active agent in said subject is in the range from about 1 µM to about 20 µM.

2. The method according to claim 1, wherein said Cmax is in the range from about 2 µM to about 10 µM.

3. The method according to claim 1, wherein the amount of said active agent is in the range from about 3 mg/kg to about 30 mg/kg.

4. The method according to claim 3, wherein the amount of said active agent is in the range from about 5 mg/kg to about 10 mg/kg.

5. The method according to claim 1, wherein said active agent is 4-methoxy-N-(3,5-bis-(1-pyrrolidinyl)-4-hydroxy benzyl)benzene sulfonamide sulfate.

6. The method according to claim 1, wherein said composition further comprises a pharmaceutically acceptable excipient.

7. The method according to claim 6, wherein said pharmaceutically acceptable excipient is selected from the group consisting of a buffer, a diluent, a stabilizer and combinations thereof.

8. The method according to claim 1, wherein said administering is by means of intramuscular injection, intravenous injection, subcutaneous injection, or oral, transdermal, inhalation, rectal, sublingual, buccal, intravaginal or nasal administration.

9. The method according claim 2, wherein said active agent is 4-methoxy-N-(3,5-bis-(1-pyrrolidinyl)-4-hydroxy benzyl)benzene sulfonamide sulfate.

10. The method according claim 3, wherein said active agent is 4-methoxy-N-(3,5-bis-(1-pyrrolidinyl)-4-hydroxy benzyl)benzene sulfonamide sulfate.

11. The method according to claim 4, wherein said active agent is 4-methoxy-N-(3,5-bis-(1-pyrrolidinyl)-4-hydroxy benzyl)benzene sulfonamide sulfate.

12. The method according to claim 2, wherein said composition further comprises a pharmaceutically acceptable excipient.

13. The method according to claim 3, wherein said composition further comprises a pharmaceutically acceptable excipient.

14. The method according to claim 4, wherein said composition further comprises a pharmaceutically acceptable excipient.

* * * * *